United States Patent [19]

Hirata et al.

[11] Patent Number: 4,923,616

[45] Date of Patent: May 8, 1990

[54] METHOD OF SEPARATING CHEMICAL COMPONENTS IN SIMULATED MOVING BED

[75] Inventors: Kentaro Hirata; Yoshio Fukui; Sadao Hayashi, all of Mie, Japan

[73] Assignee: Mitsubishi Petrochemical Company, Ltd., Tokyo, Japan

[21] Appl. No.: 248,083

[22] Filed: Sep. 23, 1988

[30] Foreign Application Priority Data

Sep. 24, 1987 [JP] Japan .................................. 62-239847
Nov. 19, 1987 [JP] Japan .................................. 62-290541

[51] Int. Cl.$^5$ .............................................. B01D 15/00
[52] U.S. Cl. ...................................... 210/676; 210/691
[58] Field of Search ................. 210/670, 676, 690–692

[56] References Cited

U.S. PATENT DOCUMENTS 3,201,491 8/1965 Stine et al. .......................... 210/676
3,956,115 5/1976 Arion ................................... 210/676
4,409,033 10/1983 Le Roy ................................ 210/278
4,747,956 5/1988 Kiniwa ................................ 210/690

Primary Examiner—Ivars Cintins
Attorney, Agent, or Firm—Oblon, Spivak, McClelland, Maier & Neustadt

[57] ABSTRACT

A method of separating chemical components in a simulated-moving-bed type continuous separator comprising a series of plural packed beds filled with adsorbent for selectively adsorbing a specific component in a crude solution, in which the packed beds are divided into three zones, and the functions assigned to the respective packed beds are successively shifted to the downstream side of the flow by the quantity of one bed by means of switching means such as a channel switching control valve comprising a stationary disc and a rotary disc rotatable thereon, thereby extracting a product solution containing a high percentage of the specific component.

8 Claims, 7 Drawing Sheets (a)

(b)

METHOD OF SEPARATING CHEMICAL COMPONENTS IN SIMULATED MOVING BED

BACKGROUND OF THE INVENTION

The present invention relates to a method of chemical separation in a simulated(pseudo) moving bed comprising a plural number of packed beds which are filled with adsorbent for adsorbing specific components contained in a crude solution and are connected in series and circulatingly. Further, the present invention relates to a channel switching control valve which is suitable for use in the method. The method of the present invention is used, for example, for separating and extracting a specific amino acid in a high concentration from a mixture solution of amino acids.

Separation of various kinds of chemical components has been performed by means of chromatography, which utilizes the difference in the adsorption properties of the components to adsorbent such as ion exchange resin, zeolite or the like. In particular, a method of separating and extracting specific components from a mixture solution by use of a simulated moving bed which is formed by connecting a plurality of adsorbent-packed beds in series and circulatingly, is well known as an effective technique.

In the conventional method of continuously separating chemical components using such a simulated moving bed, a series of packed beds are divided into four zones as shown in FIG. 11. The continuous separation in the simulated moving bed is performed by successively shifting the functions assigned to the respective packed beds to the downstream side of liquid flow, that is, the neighboring packed beds at the downstream side by use of cutoff valves incorporated in piping for connecting the beds circulatingly and an automatic valve and/or a rotary valve for switching inflow and outflow of outside solutions, such as a crude solution, a product solution and the like.

A channel switching control valve used in the conventional four-zone-type separator as described above comprises a stationary disc (a) as shown in FIG. 9 and a rotary disc (b) as shown in FIG. 10. As shown in FIG. 11, the channel switching control valve is arranged independently of the circulating flow among the packed beds. Accordingly, a special control unit is required for the opening/closing operation of specific cutoff valves corresponding to the switching of inflow/outflow of liquid. Further, the state and quantity of the circulating flow loaded on circulating pumps widely vary corresponding to the switching operation, and load on the circulating pumps must be adjusted frequently with the change of the circulating flow. Consequently, a control system using an expensive process computer is required for detecting the timing of switching operation, the change of the amount of the circulating flow due to the switching operation, and the like to thereby adjust load on the circulating pumps.

On the other hand, a method of three-zone-type continuous separation in which packed beds are reduced in number compared with the four-zone type has been proposed (in Japanese Patent Unexamined Publication No. 91205/87). The method of three-zone-type continuous separation is suited for recovering only a specific component from a crude solution, or separating and recovering a component widely different in the ability to be adsorbed, such as recovering amino acid from an enzyme reaction solution, or the like.

When an attempt to recover a specific component is made by use of the three-zone-type continuous separator, an eluent used for eluting the specific component in the desorption zone often flows in other zones. Therefore, usable eluents are limited to specific eluents which induce no interference if the eluents enter into the adsorption zone and other zones, for example, a solvent used in the crude solution.

Therefore, there is a problem that adsorbent having the too high ability to adsorb a target component or solvent having the too high elution ability for a target component cannot be used for separating and extracting the specific component in a higher concentration.

Also in the conventional three-zone-type, a special control unit is required for the opening/closing operation of specific cutoff valves for connecting the packed beds in series corresponding to the switching operation of inlets and outlets by the conventional rotary valve, to make a continuous selective effect on the respective components in the mixture material to thereby attain a continuous separating process including adsorption/separation, desorption and recovery.

SUMMARY OF THE INVENTION

An object of the present invention is to provide a method of simulated-moving-bed chemical separation used in a simulated-moving-bed type continuous separator having a series of plural packed beds filled with adsorbent for selectively adsorbing a specific component contained in a crude solution including chemical components, the last of the bed being connected to the first, and piping system including switching means for interrupting and switching connections among the beds. The method comprises the steps of: permitting the crude solution to flow in at an inlet of a front-row bend of the first zone when a series of the packed beds is divided toward the downstream side into three zones and, at the same time, interrupting the piping at a position between a rear-row bed of the first zone and a front-row bed of the second zone to thereby discharge a raffinate solution containing a low percentage of the specific component from an outlet of the rear-row bed of the first zone; permitting a first eluent to flow in at an inlet of the front-row bed of the second zone and, at the same time, interrupting the piping at a position between a rear-row bed of the second zone and a front-row bed of the third zone to thereby extract a product solution containing a high percentage of the specific component from an outlet of the rear-row bed of the second zone; permitting a second eluent to flow in at an inlet of the front-row bed of the third zone; and shifting down the position of inflow of the crude solution, the position of outflow of the raffinate solution, the position of inflow of the first eluent, the position of outflow of the product solution and the position of inflow of the second eluent to the downstream side by one bed and, at the same time, shifting down the positions of interruption corresponding to the shifting of the positions of inflow and outflow of the respective solutions, whereby a target component can be recovered in a higher concentration through the use of solvent having the elution ability for the specific component.

Another object of the invention is to provide a channel switching control valve which can perform a switching operation of liquid inlets and outlets easily and can be adapted to the case where an eluent having the ability of high desorption is prevented from flowing in zones other than the desorption zone, without use of any valve controller for controlling specific cutoff valves between packed beds corresponding to the switching operation of liquid inlets and outlets. The channel switching control valve comprising: a stationary disc having concentric paths coaxially arranged at suitable intervals about the center of the stationary disc and having downward opening channels, a first group of vertical paths annularly arranged at regular intervals in the circumferential direction with a larger radius than those of the concentric paths and serving as downward opening channels, and a second group of vertical paths annularly arranged at regular intervals in the circumferential direction with a larger radius than that of the circle of the first group and serving as downward opening channels to form a number, of counterparts corresponding to the vertical paths of the first group; and a rotary disc having junction paths comprising first junction paths arranged at suitable positions corresponding to the positions at which the vertical paths of the first and second groups are formed in the stationary disc, a number, l, of first paths extending outward respectively from the first junction paths to each pair of the second junction paths corresponding to each pair of vertical paths selected from the first and second groups, a number, 2k, of second paths extending outward respectively from the first junction paths to one of each pair of the second junction paths corresponding to each pair of the vertical paths selected from the first and second groups, and a number, j, of third paths to connect respectively one pair of the second junction paths to each other, the rotary disc being rotatable on the stationary disc and the numbers, j, k, l, m, and n satisfying the equations $m = j + k + l$ and $n = 2k + l (k \neq 0)$, where n is an integer of 4, 5 or 6, and m is an integer of 3 or more.

DETAILED DESCRIPTION OF THE INVENTION

A separating method according to the present invention will be described in detail representatively using one example thereof used for separation of components A and B, with reference to the accompanying drawings.

Figure 1:
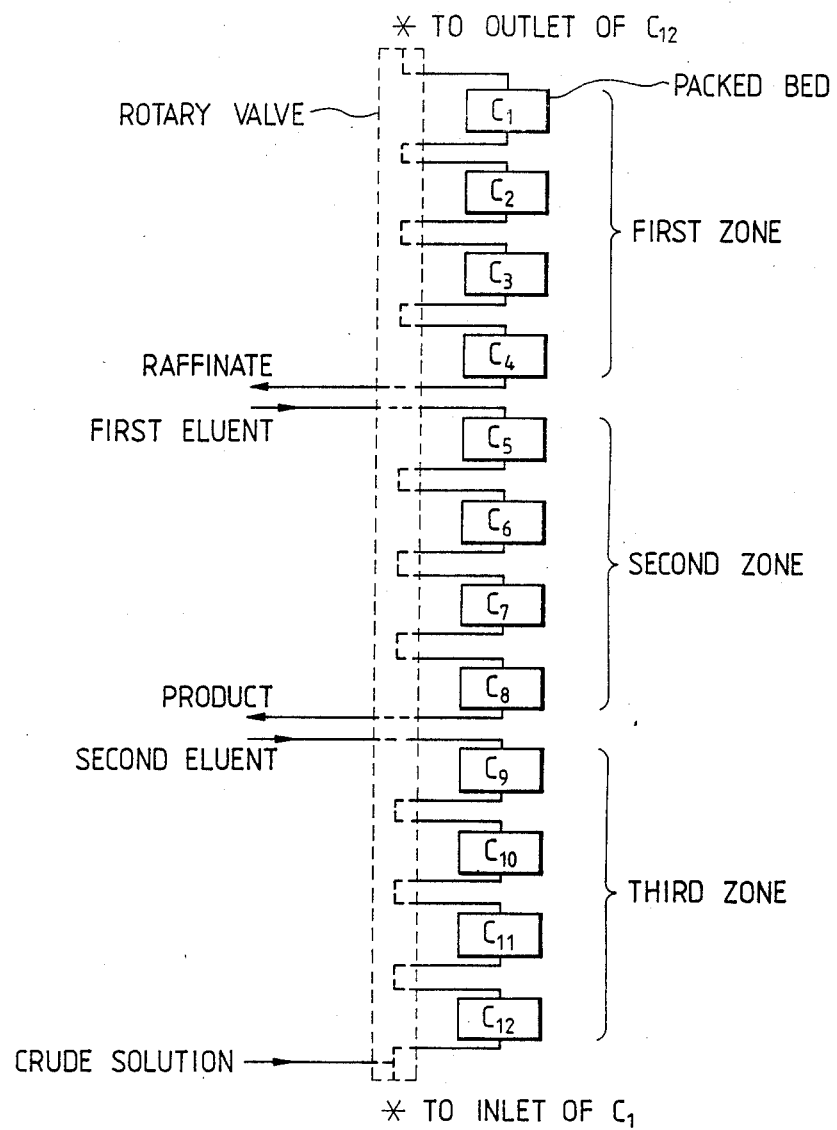
FIG. 1 is an explanatory diagram for showing a flow of a series of packed beds in the simulated moving bed according to the present invention.
Figure 2:
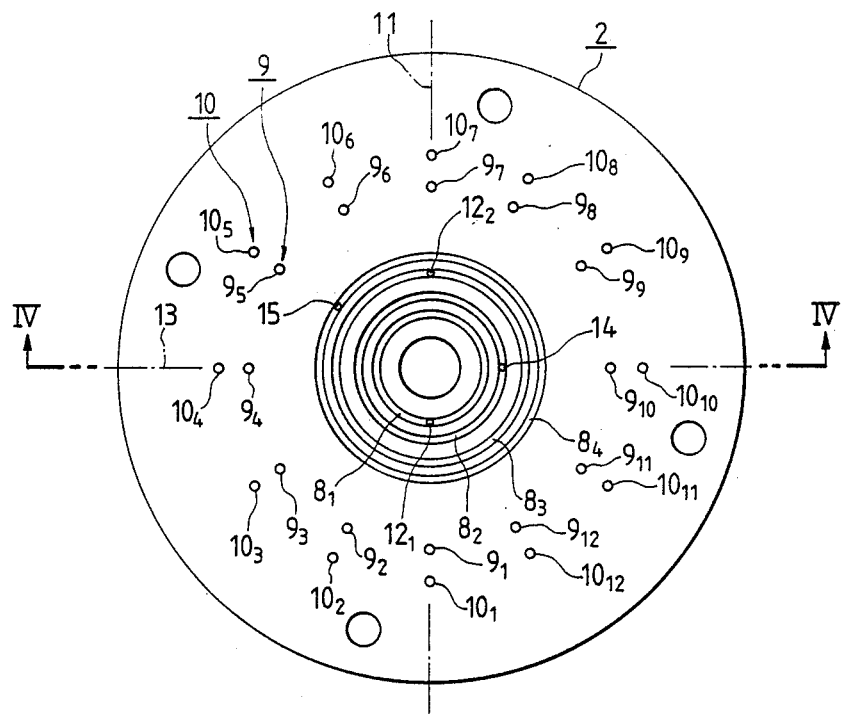
FIG. 2 is a plan view of a stationary disc used in the method according to the present invention.

FIG. 1 is an explanatory diagram for showing a flow of a simulated-moving-bed type continuous separator used in the present invention. Twelve packed beds $C_1$ to $C_{12}$, which are filled with adsorbent for selectively adsorbing a component A contained in a crude solution, are series-connected by piping through a rotary valve as shown by the broken line in FIG. 1. The rotary valve has piping-cutoff means and switching control means as an inside mechanism for cutting off the piping and switching the piping to outside piping. The rotary valve, preferably, may be a channel switching control valve which will be described hereinafter. Further, the last packed bed $C_{12}$ is connected to the first packed bed $C_1$ by piping through the rotary valve, thus to form a circulating simulated-moving-bed type continuous separator. In the case where the channel switching control valve as shown in FIG. 2 is used in the invention, piping for connection between the packed beds $C_4$ and $C_5$ and between the packed beds $C_8$ and $C_9$ is separated from the piping which is circulated by the inside mechanism of the rotary valve, and is adapted to the positions to be connected to the outside piping.

In the case where a single-connection-type rotary valve having no inside control mechanism and having only a mechanism for switching the inlet and outlet of liquid flow is used in the invention, the method according to the invention can be effectuated, for example, by using a piping system including electromagnetic valves and a valve opening control unit in combination.

FIG. 1 also shows the case where a pseudo moving bed is formed by dividing a series of packed beds $C_1$ to $C_{12}$ equally into three zones as a typical example, in which the beds $C_1$ to $C_4$ are assigned to a first zone, the beds $C_5$ to $C_8$ are assigned to a second zone, and the beds $C_9$ to $C_{12}$ are assigned to a third zone.

In a condition as shown in FIG. 1, the crude solution is introduced into the bed $C_1$ through the rotary valve. As the mixture of components A and B contained in the crude solution is moved downward by liquid flow, the component A is selectively adsorbed by adsorbent filled in the beds. On the other hand, the component B which is little adsorbed by the adsorbent is moved more downward.

In this state, the component B is separated from this system at the bed $C_4$ through the rotary valve and flows out in the form of a raffinate solution containing a high percentage of the component B or in other words containing a low percentage of the component A. Further, a first eluent is introduced into the bed $C_5$ through the rotary valve. The eluent comprises solvent which has a high elution ability for the component A. The component A having been adsorbed by the adsorbent is easily eluted by the introduction of the first eluent, so that the eluted component A moves downward. A product solution containing a high percentage of the eluted component A is separated from this system through the rotary valve and flows out. Since piping between the beds $C_8$ and $C_9$ is cut off in this case, the first eluent does not flow into the third zone and the first zone.

Still further, a second eluent provided as a solution of the same solvent as that of the crude solution is introduced into the bed $C_9$ through the rotary valve. In continuous separation, the component B which exists in the beds $C_9$ to $C_{12}$ as holdings of the beds due to the crude solution supplied in a period previous to the connection condition as shown in FIG. 1 is fed downward by the introduction of the second eluent. Since the component B is not brought into the second zone, that is, elution zone, in spite of the beds shifted by switching, an excessive amount of the component B can be prevented from mixing in the product solution.

After a certain predetermined time, the rotary valve is rotated by an angle corresponding to one bed. Then the crude solution is introduced into the bed $C_2$ through the rotary valve, so that the raffinate solution is drawn out of this system at the bed $C_5$. The first eluent is introduced into the bed $C_6$ so that the product solution is drawn out of this system at the bed $C_9$. Further, the second eluent is introduced into the bed $C_{10}$.

The rotation of the rotary valve can be made almost in an instant so that a switching operation is carried out with every predetermined time to shift down the positions of inflow and outflow of the respective solutions successively to the downstream side.

The first, second and third zones are shifted down successively to the downstream side by the aforementioned procedure so that the operation can be made as if it were made in a moving bed. Accordingly, the product solution having a high concentration of the component A can be taken out continuously.

Although this embodiment has shown the case where each zone is composed of four beds, it is a matter of course that the number of beds belonging to each zone can be changed corresponding to the length of the adsorption zone, the degree of difficulty of elution and the like. The number of components contained in the crude solution may be two or more. In short, the method of the present invention is a method for separating two groups as a product solution and a raffinate solution by use of the difference in adsorption force by absorbent and for taking out the product solution in a high concentration.

As the present invention can employ adsorbent having the relatively higher ability to adsorb the target component and solvent having the relatively higher elution ability for the target component compared with the conventional three-zone-type simulated moving bed, the resulting product solution can be take out with a high concentration of the target component. Accordingly, the invention is well adapted for separation and extraction of a specific amino acid from a mixture solution of amino acids.

Further, variable charges and fixed charges in cost of equipment on the whole of a separating and purifying system can be reduced, compared with the prior art.

Still further, the packed beds can be connected in series through piping to form a circulating piping system by using a channel switching control valve which will be described later in detail, and therefore the piping system can be simplified in the structure.

In the channel switching control valve according to the present invention, the number, m, of vertical paths in each of the first-and second-step annularly-arranged vertical path groups, for example, $9_1$–$9_{12}$ and $10_1$–$10_{12}$ in a stationary disc as shown in FIG. 2, is an arbitrary integer of 3 or more corresponding to the number of the packed beds in the simulated-moving-bed type separator. Any suitable even number may be used for m from the point of view of manufacturing technique and, in general, an even number of 10 to 20, particularly, 12, may be widely used for from the point of view of separating each component or handling the valve.

In general, the pairs of the annularly-arranged vertical paths are connected respectively to the inlet-side and outlet-side piping of the packed beds along the circulating flow. In other words, the outflow liquid of each packed bed is fed to the next bed through the channel switching control valve according to the present invention.

The concentric paths, for example $8_1$–$8_4$ of the stationary disc 2 as shown in FIG. 2, are provided to control the circulating flow in the case where lines of inflow and outflow, such as lines for feeding the crude solution and eluents into a system composed of packed beds, extracting the product solution and raffinate solution out of the system and the like, and circulating pumps are provided. The number of the concentric paths can be selected arbitrarily from integers not less than 4, and in general, integers of 4 to 8 from the point of view of separating two components.

In the case where the stationary disc is used in the three-zone-type pseudo-moving-bed continuous separator according to this invention, the number, n, is selected from integers of 4 to 6. The number, n, is preferably 5 in the method according to the present invention.

Further, a rotary disc of the channel switching control valve of this invention has junction paths comprising first junction paths arranged at suitable positions on said concentric paths of the stationary disc and second junction paths arranged at the positions at which the second junction paths communicate with the first-and second-step annularly-arranged vertical paths formed in the stationary disk, a number (l) of first paths extending outwardly from the first junction paths to respective pairs of the second junction paths which correspond to respective pairs of the vertical paths selected from the first-and second-step annularly-arranged vertical path groups, thereby to connect each of the first junction paths to each pair of the second junction paths, and a number (2k) of second paths each extending outwardly from the corresponding one of the first junction paths to one of each pair of the second junction paths thereby to connect each of the first junction paths to one of each pair of the second junction paths. The relation of the number (n) of the concentric paths of the stationary disk and the numbers 2k and l as described above is expressed as $n = 2k + l \geq 4$. In general, the positions of the first junction paths on the concentric paths are determined from the point of view of easiness in construction and handling property so that the respective pairs of the second paths (2k) are arranged to be relatively near and, however, the first paths are arranged to be dispersed. The first and second paths for connecting the junction paths are formed so that the connection can be made at the shortest distance.

One embodiment of the channel switching control valve according to the present invention will be described with reference to FIGS. 3, 4 and 5.

Figure 4:
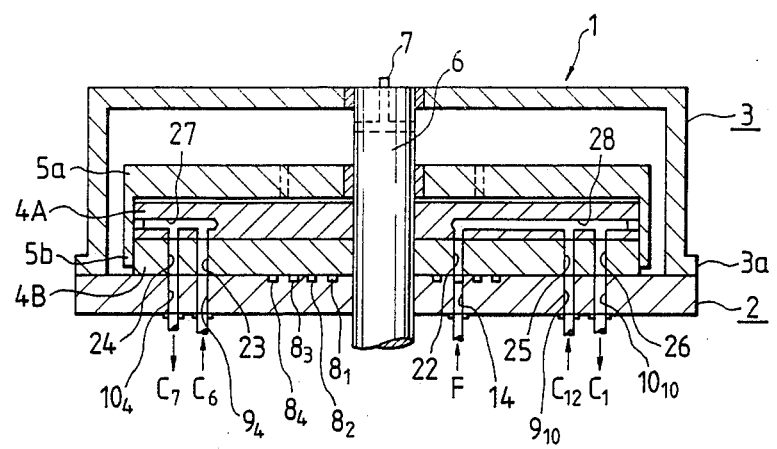
FIG. 4 is a sectional view taken along the line III—III as shown in FIGS. 2 and 3.

Referring to FIG. 4, there is shown a channel switching control valve 1 of the present invention, in which the bottom of a circumferential wall portion 3a of an downward-open cylindrical casing 3 is fixed onto the upper surface of a stationary disc 2. A rotary disc 4 and a sealing 5 are arranged within an inside space formed by the stationary disc 2 and the casing 3. A driving shaft 6 is inserted into the respective center portions of the stationary disc 2, the rotary disc 4, the sealing 5 and the casting 3 so that the driving shaft 6 can be freely rotated by a driving mechanism (not shown).

In the drawing, the rotary disc 4 comprises an upper part 4A and a lower part 4B of Teflon to thereby form one body and is mounted to the driving shaft 6 so that it is rotated together with the driving shaft 6. The sealing 5 shaped like a reverse saucer has a bottom wall 5a and a circumferential wall 5b which are in frictional contact with the upper surface and circumferential surface of the rotary disc 4, respectively, to secure the sealing of the rotary disc 4 through pressured air fed from an air duct 7 of the driving shaft 6 to the inside space of the casing 3.

As shown in FIG. 2, the stationary disc 2 is provided with a first concentric path $8_1$, a second concentric path $8_2$, a third concentric path $8_3$ and a fourth concentric path $8_4$ which are arranged to form coaxial circles with gradually enlarged radii about the center of the stationary disc; a first-step annularly-arranged vertical path group 9 consisting of twelve vertical paths $9_1$ to $9_{12}$ which are arranged at equal circumferential intervals on a circle with a large radius than that of the fourth concentric path $8_4$ and are open downward; a second-step annularly-arranged vertical path group 10 consisting of twelve vertical paths $10_1$ to $10_{12}$ which are arranged in the same radial-direction position as the first-step annularly-arranged vertical path group 9 and at the outside thereof; downward-open flow paths $12_1$ and $12_2$ provided opposite to each other with respect to the center and in the first concentric path $8_1$ and the third concentric path $8_3$; a downward-open flow path 14 provided in the second concentric path $8_2$ at a position on a line perpendicular to the flow paths $12_1$ and $12_2$; and a downward-open flow path 15 provided in the fourth concentric path $8_4$.

Figure 3:
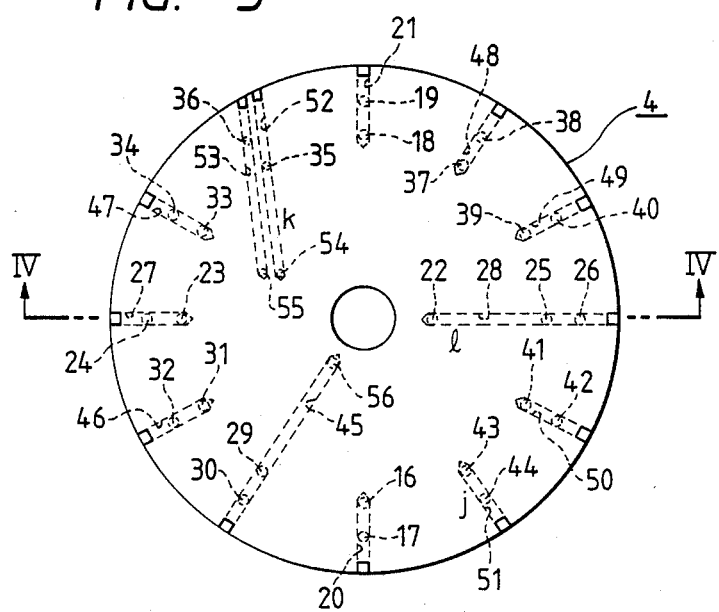
FIG. 3 is a plan view of a rotary disc used in the method of the present invention.

As shown in FIG. 3, the rotary disc 4 is provided with a first path 20 and a second path 21 corresponding to the positions for connecting two pairs of junction paths (16, 17) and (18, 19) corresponding to two pairs of vertical paths ($9_1$, $10_1$) and ($9_7$, $10_7$) selected from the first- and second-step annularly-arranged vertical path groups 9 and 10 of the stationary disc 2; and a third path 27 and a fourth path 28 extending radially outward from a junction path 22 corresponding to the flow path 14 of the second concentric path $8_2$ so as to be perpendicular to the paths 20 and 21, the paths 27 and 28 corresponding to the positions for connecting two pairs of junction paths (23, 24) and (25, 26) corresponding to two pairs of vertical paths ($9_4$, $10_4$) and ($9_{10}$, $10_{10}$) selected from the first- and second-step annularly-arranged vertical path groups 9 and 10, the fourth path 28 being formed as a liner path to connect the junction paths 25, 26 and 22.

Junction paths 29, 30, 31, 32, 33, 34, 35, 36, 37, 38, 39, 40, 41, 42, 43 and 44 which correspond to the vertical paths $9_2$, $10_2$, $9_3$, $10_3$, $9_4$, $10_4$, $9_5$, $10_5$, $9_6$, $10_6$, $9_7$, $10_7$, $9_8$ and $10_8$ selected from the first- and second-step annularly-arranged vertical groups 9 and 10 of the stationary disc 2 are formed. The rotary disc 4 further has a fifth path 45, a sixth path 46, a seventh path 47, an eight path 48, a ninth path 49, a tenth path 50 and an eleventh path 51 extending radially outward and connecting the pairs of junction paths (29, 30), (31, 32), (33, 34), (37, 38), (39, 40), (41, 42), (43 and 44) except the pair of junction paths (35 and 36).

Further, a fourteenth path 52 passing through the junction path 35 and a fifteenth path 53 passing through the junction path 36 are provided in parallel to each other. A junction path 54 formed at the central side of the fourteenth path 52 communicates with the vertical path $12_2$. A junction path 55 formed at the central side of the fifteenth path 53 communicates with the vertical path 15. The junction path 22 communicates with the vertical path 14. A junction path 56 formed on an extension of the seventh path 45 communicates with the vertical path $12_1$.

According to the construction of the channel switching valve, when the rotary disc 4 is located as shown in FIG. 4 relative to the stationary disc 2, liquid supplied from the vertical path $9_4$ passes through the junction path 23, the second path 27, and the junction path 24 and exhausted from the vertical path $10_4$.

Figure 5:
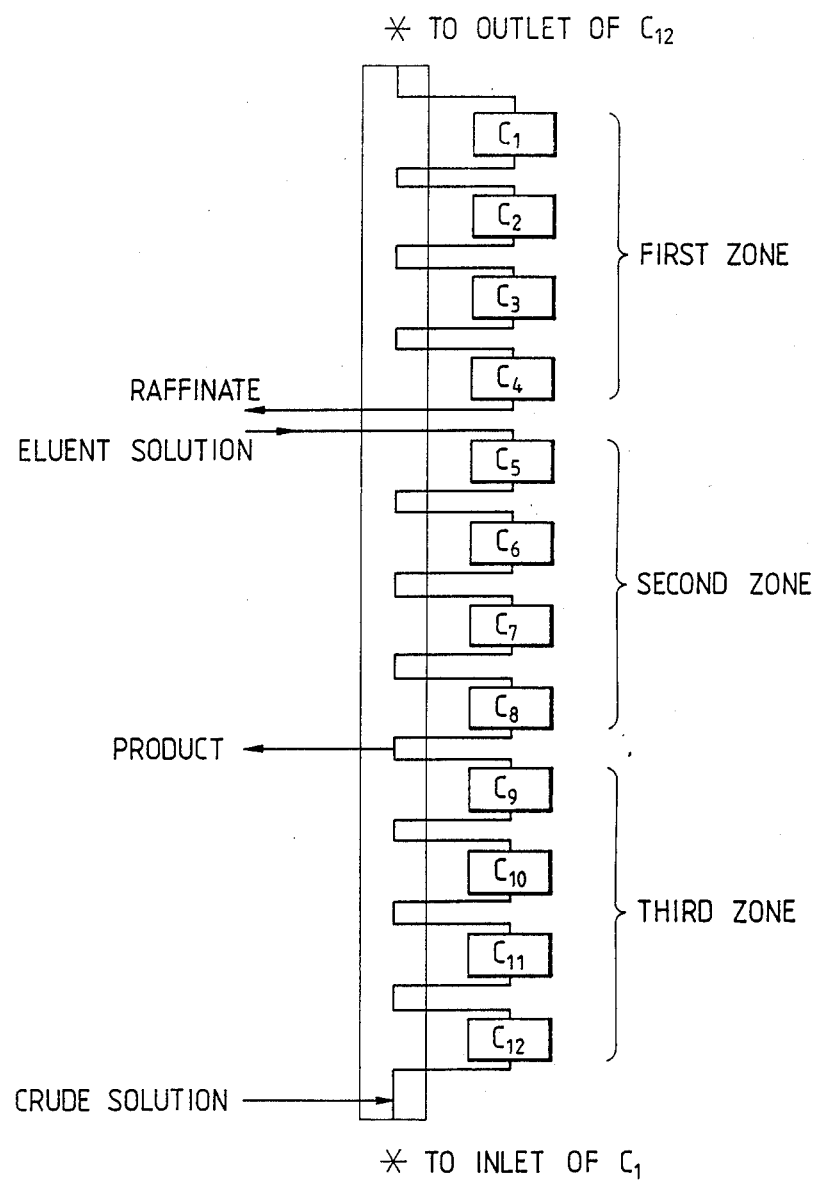
FIG. 5 is an explanatory diagram in the case where the method according to the present invention is applied to a simulated-moving-bed type chromatographic separator.

The invention as to the case where the valve is adapted to a simulated-moving-bed type continuous separator as shown in FIG. 5 to operate a mixture material (F) in a cycle of adsorption separation (R), desorption (O) and recovery (E) will be described in detail.

Referring to FIG. 2 through FIG. 5, the rotary disc 4 is arranged to rotate counterclockwise in the condition that liquid can be exhausted from $C_{12}$ and can be introduced from $C_1$ when the stationary disc 2 is provided with the first-step annularly-arranged group of vertical paths $9_1$ to $9_{12}$ as outlets of the packed beds $C_1$ to $C_{12}$ and with the second-step annularly-arranged group of vertical paths $10_1$ to $10_{12}$ as inlets thereof.

The crude solution together with the flow from the packed bed $C_{12}$ is fed to the packed bed $C_1$, via the flow path 14, the second concentric path $8_2$, the junction path 22 of the rotary disc 4, and the ninth path 28.

The raffinate from the packed bed $C_4$ is drawn out from the flow path $12_2$ via the third concentric path $8_3$. The eluent is fed to the packed bed $C_5$ via the fourth concentric path $8_4$.

Part of the flow from the packed bed $C_8$ is fed to the packed bed $C_9$ from the path 45 of the rotary disc 4 and other part is extracted from the first concentric path $8_1$, as a product.

The switching operation for the inlets and outlets is performed by rotating the rotary disc 4 counterclockwise by an angle of 30°, so that the position of inflow of the crude solution and the position of outflow of the product can be shifted to the downstream side by the quantity of one bed; for example, the crude solution and the product are fed to the packed beds $C_2$ and $C_9$, respectively.

The flow system and the switching control system in the packed beds $C_1$ to $C_{12}$ are illustrated in Table (1) in the case where the rotary disc 4 is in the positional state as shown in FIG. 4.

These systems are illustrated in Table (2) in the case where the rotary disc 4 is counterclockwise rotated by an angle of 30° from the position thereof as shown in FIG. 4.

TABLE (1)

| | Bed/Tank | | F | $C_{12}$ | $C_8$ |
|---|---|---|---|---|---|
| flow direction | Stationary disc | Vertical path | 14 | $9_{10}$ | $9_2$ |
| | | Concentric path | $8_2$ | — | — |
| | Rotary disc | Junction path | 22 | 25 | 29 |
| | | Path | 28 | | 45 |
| | | Junction path | 26 | 56 | 30 |
| | Stationary disc | Concentric path | — | $8_1$ | — |
| | | Vertical path | $10_{10}$ | $12_1$ | $10_2$ |
| | Bed/Tank | | $C_1$ | E | $C_9$ |

TABLE (2)

| flow direction | Bed/Tank | | F | $C_1$ | $C_9$ |
|---|---|---|---|---|---|
| | Stationary disc | Vertical path | 14 | $9_9$ | $9_1$ |
| | | Concentric path | $8_2$ | — | — |
| | Rotary disc | Junction path | 22 | 25 | 29 |
| | | Path | | 28 | 45 |
| | | Junction path | | 26 | 56 | 30 |
| | Stationary disc | Concentric path | — | $8_1$ | — |
| | | Vertical path | $10_9$ | $12_1$ | $10_1$ |
| | Bed/Tank | | $C_2$ | E | $C_{10}$ |

Referring to Table (1), for example, the mixture material (F) from a supply line passes through the flow path 14 and concentric path $8_2$ of the stationary disc 2 in the channel switching control valve 1 according to the present invention and enters into the junction path 22 and the path 28 of the rotary disc 4. The flow of liquid from the bed $C_{12}$ passes through the vertical path $9_{10}$ of the stationary disc 2 and joins with the flow from the junction path 25 of the rotary disc 4 so that the resulting flow is fed to the bed $C_1$ through the junction path 26. Since the bed $C_8$ is connected to the bed $C_9$ in series, part (E) of the flow from the bed $C_8$ is drawn out of the channel switching control valve 1.

When the rotary disc 4 rotates by an angle of 30° after a predetermined time, the mixture material (F), as shown in Table (2), joins with the flow of the bed $C_1$ and reaches the bed $C_2$ and, at the same time, the bed $C_9$ is series-connected to the bed $C_{10}$, so that part(E) of the flow from the bed $C_9$ is drawn out of the channel switching control valve 1. When the rotary disc 4 rotates by an angle of 90°, the mixture material (F) joins with the flow of the bed $C_3$ and reaches the bed $C_4$, so that part (E) of the flow from the bed $C_{11}$ is drawn out of the channel switching control valve 1.

When the rotary disc 4 makes one turn to return its original position according to the aforementioned procedure, a cycle of separating process is accomplished while the functions of the beds $C_1$ to $C_{12}$ are always changed.

This embodiment shows the case where the concentric paths of the stationary disc are used as a first concentric path through a fourth concentric path connected to the respective tanks; each of the first- and second-step annularly-arranged vertical path groups is equally divided into 12; and the junction paths and other paths of the rotary disc are established correspondingly to the aforementioned condition. However, it is a matter of course that the invention is not limited to the specific embodiment and that various changes and modifications may be made in the invention without separating from the spirit thereof.

A second embodiment of the channel switching control valve used in the method of the present invention is described with reference to FIGS. 6 through 8.

A stationary disc 58 of the channel switching control valve 57 of the second embodiment is provided by adding a fifth concentric path $8_5$ and a flow path 59 to the construction of the stationary disc 2 of the channel switching control valve 1 of the first embodiment as described above. A rotary disc 60 of the channel switching control valve 57 of the second embodiment is provided by adding a twelfth path 62 to the construction of the rotary disc 4. The twelfth path 62 makes a connection between a junction path 61 communicating with the second concentric path $8_2$ and the junction path 30 and intersects the seventh path 45.

According to the channel switching control valve 57 of the second embodiment of the present invention, the all quantity of the product flow from the packed bed $C_8$ is drawn out through the concentric paths. Solvent which induces no interference if it enters into the adsorption zone, in general, the same solvent as that used in the crude solution is fed to the packed bed $C_9$ through the vertical path of the stationary disc 58 from the junction path formed in the inside path of the rotary disc 60 through the second concentric path $8_2$. Accordingly, the eluent from the packed bed $C_5$ never flows into the packed bed $C_9$ and the subsequent packed beds. By rotating the rotary disc 60 conterclockwise by an angle of 30°, the positions of inlets and outlets are shifted to the downstream side successively.

Further, the channel switching control valve according to the second embodiment of the invention has a stationary disc provided with two steps of annularly-arranged vertical path groups, and a rotary disc provided with one pair or more of paths for connecting junction paths on concentric paths and one-side portions of one pair of junction paths corresponding to annularly-arranged vertical paths, to thereby make switching control of inflow/outflow between the outside and respective packed bed easy. Accordingly, a cycle of separating process can be easily repeated without troublesome process of detecting the timing of channel switching and changing flow rate frequently, while the functions of the beds are suitably changed.

EXAMPLE

To make the effect of the present invention clearer, the method of three-zone-type separation will be described in detail with reference to the following example.

Figure 6:
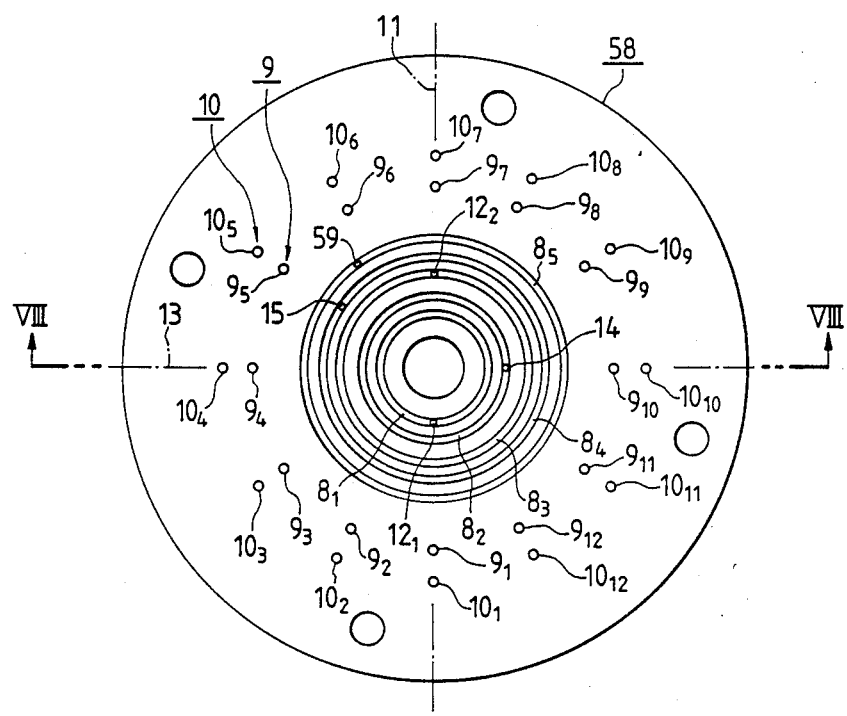
FIG. 6 is a plan view of another stationary disc used in the method according to the present invention.
Figure 7:
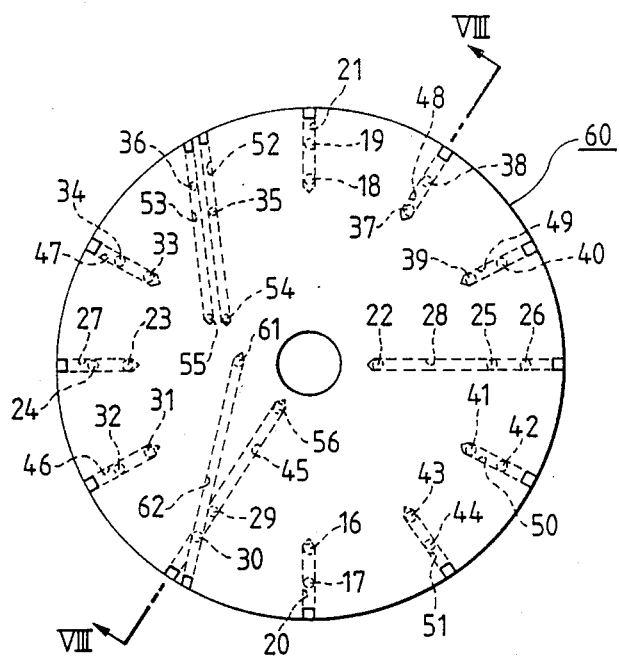
FIG. 7 is a plan view of another rotary disc used in the method of the present invention.
Figure 8:
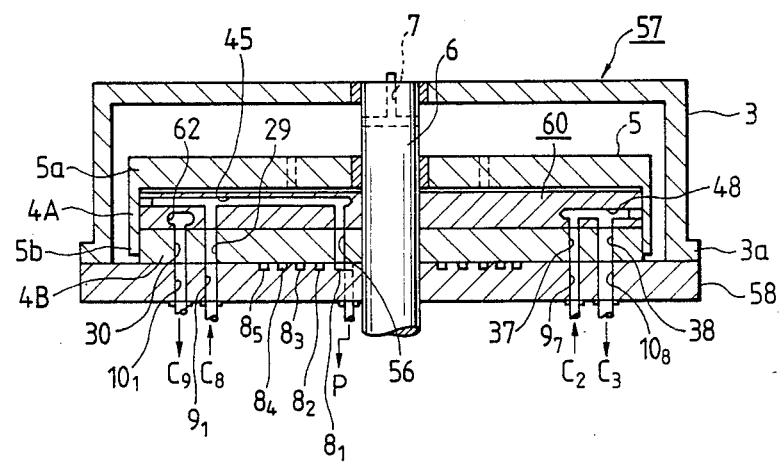
FIG. 8 is a sectional view taken along the line VII—VII as shown in FIGS. 6 and 7.
Figure 9:
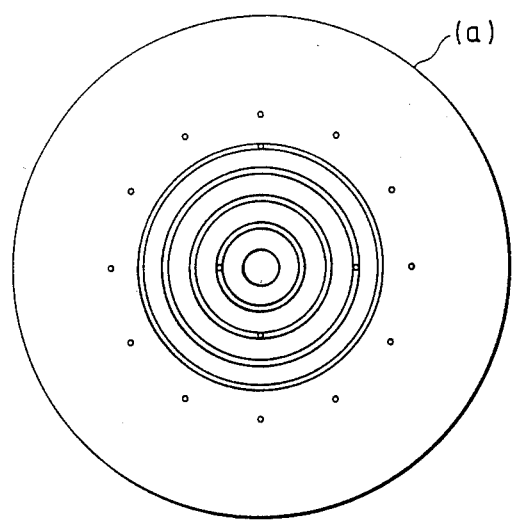
FIG. 9 is a plan view of a stationary disc in a conventional channel switching control apparatus.
Figure 10:
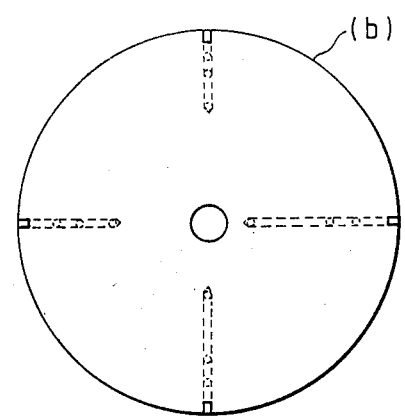
FIG. 10 is a plan view of a rotary disc in the conventional channel switching control apparatus.
Figure 11:
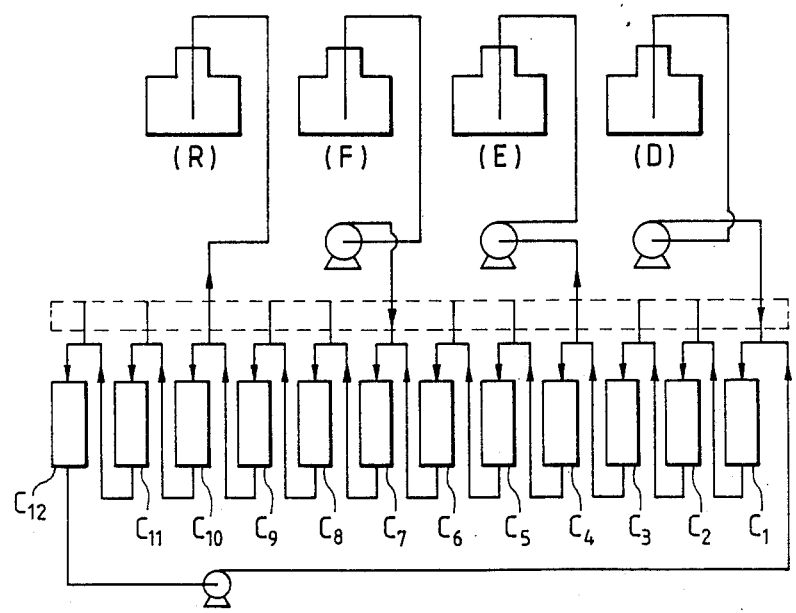
FIG. 11 is an explanatory diagram in the case where the conventional method is applied to a four-zone-type simulated-moving-bed chromatographic separator.

An apparatus for simulated-moving-bed type continuous separation in which twelve packed beds ($C_1$, $C_2$, ..., $C_{12}$) each having an inner diameter of 0.8 cm and a length of 8 cm were connected circulatingly as shown in FIG. 1 by piping through a rotary valve having an inside control mechanism as shown in FIGS. 6 to 8, was used. The first zone was composed of five beds, the second zone was of four beds, and the third zone was of three beds. The respective beds were filled with synthetic adsorbent (trade name: DIAION HP-20; Mitsubishi Chemical Industries, Ltd.). A mixture aqueous solution containing L-tryptophan and D,L-serine in the following proportion, as a crude solution, was introduced into the front portion of the bed $C_1$, so that the resulting solution (raffinate solution) containing D,L-serine being little adsorbed by the adsorbent was taken out at the rear portion of the bed $C_5$. A 4.5% concentration of aqueous ammonia as a first eluent was introduced into the front portion of the bed $C_6$, so that the resulting solution (product solution) containing a high percentage of L-tryptophan being easily adsorbed by the adsorbent was taken out at the rear portion of the bed $C_9$. Further, water as a second eluent was introduced into the front portion of the bed $C_{10}$.

After a predetermined time, the rotary valve was rotated by the quantity of one bed. The crude solution was introduced into the front portion of the bed $C_2$, so that the raffinate solution was taken out at the rear portion of the bed $C_6$. The first eluent, that is, aqueous ammonia, was introduced into the front portion of the bed $C_7$, so that the product solution was taken out at the rear portion of the bed $C_{10}$. Further, the second eluent, that is, water, was introduced into the front portion of the bend $C_{11}$.

The aforementioned procedure was repeated to shift the positions of introduction and extraction of the solutions along the flow of liquid successively. Metering pumps were used for supply of the crude solution, first eluent and second eluent; column circulating pumps were not used.

The composition of the crude solution and the operational condition were as follows.

| Crude solution | L-tryptophan | 10 g/l |
| | D,L-serine | 10 g/l |
| Moving cycle | | 362 sec. |
| First eluent (4.5% aqueous ammonia) | | |
| | rate of inflow | 100 ml/HR |
| Product solution | rate of outflow | 100 ml/HR |
| Rate of inflow of the crude solution | | 150 ml/HR |
| Second eluent (water) | rate of inflow | 60 ml/HR |
| Raffinate solution | rate of outflow | 210 ml/HR |

When the distribution in concentration of the two components in the apparatus became stationary, the L-tryptophan concentration of the product solution was 15.13 g/l and the D,L-serine concentration thereof was 1.85 g/l. On the other had, the L-tryptophan concentration of the raffinate solution was 0.04 g/l and the D,L-serine concentration thereof was 8.08 g/l.

Figure 12:
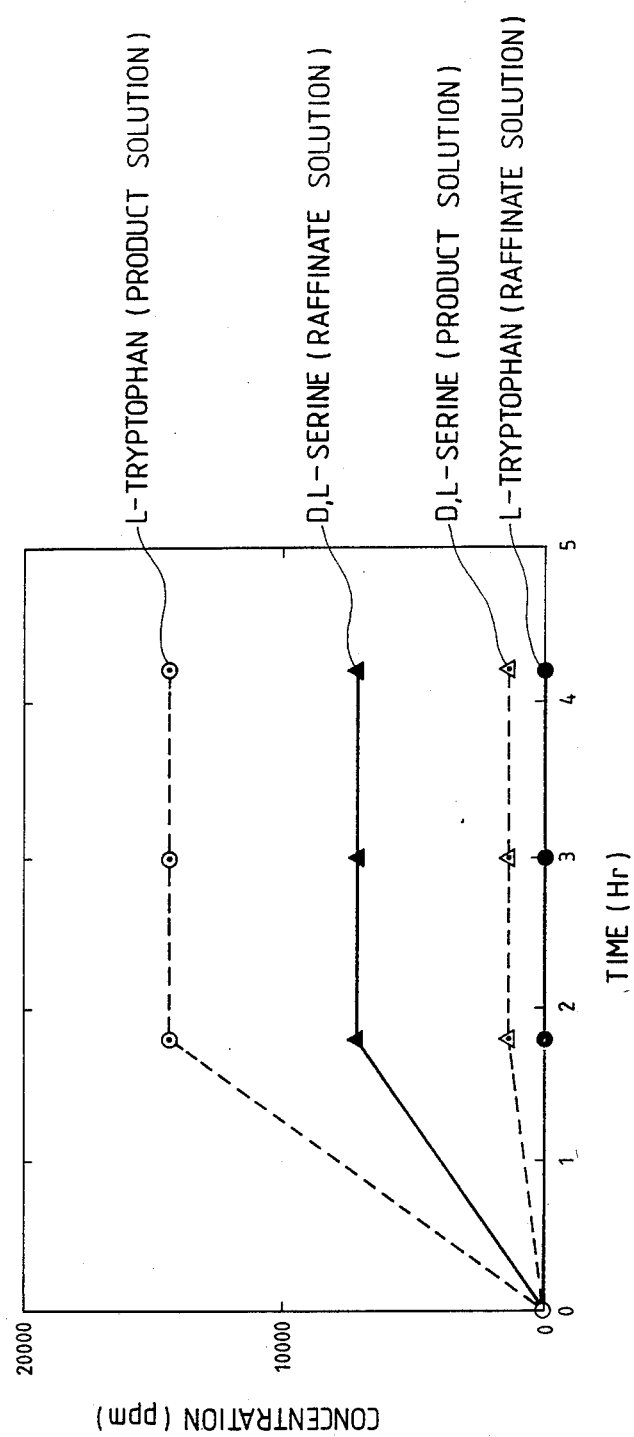
FIG. 12 is a graph for showing the changes in concentration with time, of components in the product solution and raffinate solution in an experiment.

The changes with the passage of time, of the respective components in the product solution and the raffinate solution are shown in FIG. 12.

What is claimed is:

1. A method of separating chemical components in a simulated-moving-bed continuous separator having a series of plural packed beds filled with adsorbent for selectively adsorbing a specific component contained in a crude solution including plural chemical components, said packed beds being divided toward the downstream side into three zones, the last of said packed beds being connected to the first, and a piping system including switching means for interrupting and switching connections among each bed, said method comprising:
    (a) introducing a crude solution to an inlet of a front-row bed of a first zone of said packed beds and, at the same time, interrupting the piping at a position between a rear-row bed of the first zone and a front-row bed of a second zone, to thereby discharge a raffinate solution containing a less than substantial percentage of said specific component from an outlet of the rear-row bed of the first zone;
    (b) introducing a first eluent to an inlet of the front-row bed of the second zone and, at the same time, interrupting the piping at a position between a rear-row bed of the second zone and a front-row bed of the third zone to thereby extract a product solution containing a substantial percentage of said specific component from an outlet of the rear-row bed of the second zone;
    (c) introducing a second eluent to an inlet of the front-row bed of the third zone; and
    (d) shifting down the position of inflow of said crude solution, the position of outflow of said raffinate solution, the position of inflow of said first eluent, the position of outflow of said product solution and the position of inflow of said second eluent to the downstream side by one bed and, at the same time, shifting down the interruption positions of said piping systems in correspondence with the shifting of the positions of inflow and outflow of the respective solutions.

2. The method according to claim 1, wherein said second eluent is the same solvent as that used in said crude solution.

3. The method according to claim 1, wherein said crude solution is an aqueous solution.

4. The method according to claim 1, said chemical components contained in said crude solution are amino acids.

5. The method according to claim 1, wherein said first eluent is aqua ammonia.

6. The method according to claim 1, wherein said switching means comprises a rotary valve.

7. The method according to claim 6, wherein said rotary valve is a channel switching control valve comprising a stationary disk having five concentric paths coaxially arranged about the center of said stationary disk and having downward opening channels therein, a first group of vertical paths annularly arranged in the circumferential direction with a larger radius than those of said concentric paths and serving as downward opening channels, and a second group of vertical paths annularly arranged in the circumferential direction with a larger radius than that of the circle of said first group and serving as downward opening channels to form a number, m, of counterparts to said vertical paths of said first group, and a rotary disk having junction paths comprising first junction paths arranged on said concentric paths of said stationary disk and second junction paths arranged at positions corresponding to the positions at which said vertical paths of said first and second groups are formed in said stationary disk, a first path extending outwardly from one of said first junction paths to one pair of said second junction paths corresponding to one pair of vertical paths selected from said first and second groups, two pairs of second paths extending outward respectively from the other junction paths of said first junction paths to one of each pair of said second junction paths corresponding to each pair of vertical paths selected from said first and second groups, and a number, j, of third paths to connect, respectively, each pair of the residual junction paths of said second junction paths, said rotary disk being rotatable on the stationary disk and said numbers, j and m, satisfied in the equation $m = j + 3$.

8. A method according to claim 7, wherein m is 12 or 16.

* * * * *

UNITED STATES PATENT AND TRADEMARK OFFICE
CERTIFICATE OF CORRECTION

PATENT NO. : 4,923,616
DATED      : May 8, 1990
INVENTOR(S): Kentarou HIRATA, et al It is certified that error appears in the above-identified patent and that said Letters Patent is hereby corrected as shown below:

On the title page:

The first inventor's name has been misspelled, it should read
          --Kentarou HIRATA--

Signed and Sealed this

Eleventh Day of June, 1991

*Attest:*

HARRY F. MANBECK, JR.

*Attesting Officer*      *Commissioner of Patents and Trademarks*